United States Patent [19]

DiMatteo

[11] 4,134,400

[45] Jan. 16, 1979

[54] STRAP FOR A PROTECTIVE DEVICE

[76] Inventor: Frank J. DiMatteo, 501 Sunnyfield Dr., Monroeville, Pa. 15146

[21] Appl. No.: 778,868

[22] Filed: Mar. 18, 1977

Related U.S. Application Data

[63] Continuation-in-part of Ser. No. 696,740, Jun. 16, 1976, Pat. No. 4,043,329.

[51] Int. Cl.² .............................................. A61F 5/40
[52] U.S. Cl. ..................................... 128/158; 128/161
[58] Field of Search .................. 128/132 R, 158, 160, 128/161

[56] References Cited

U.S. PATENT DOCUMENTS

| | | | |
|---|---|---|---|
| 1,030,224 | 6/1912 | Bauer | 128/158 |
| 1,063,062 | 5/1913 | Quenzer | 128/158 X |
| 1,381,254 | 6/1921 | Thorp | 128/160 |
| 1,421,077 | 6/1922 | Goldsmith | 128/160 |
| 1,686,943 | 10/1928 | Tritch | 128/160 |
| 2,266,062 | 12/1941 | Montmarquet | 128/160 |

*Primary Examiner*—Lawrence W. Trapp
*Attorney, Agent, or Firm*—Robert D. Yeager

[57] ABSTRACT

A jockstrap is provided for holding a protective device in place on a human body. The protective device is a rigid cup having sufficient volume to enclose the male genitals. The protective device, when positioned properly, extends from the area above the male genitals, underneath the abdomen to a point in the vicinity of the wearer's rectum. The jockstrap includes a waist band, two straps attached to the waist band and a pouch for holding the protective device attached to the waistband and the two straps. The pouch extends from an area above the wearer's genitals, below the wearer's abdomen, to a point near the wearer's rectum. The jockstrap holds the protective device against the wearer's body in such a manner that the wearer's genitals are protected from blows from any direction.

7 Claims, 8 Drawing Figures

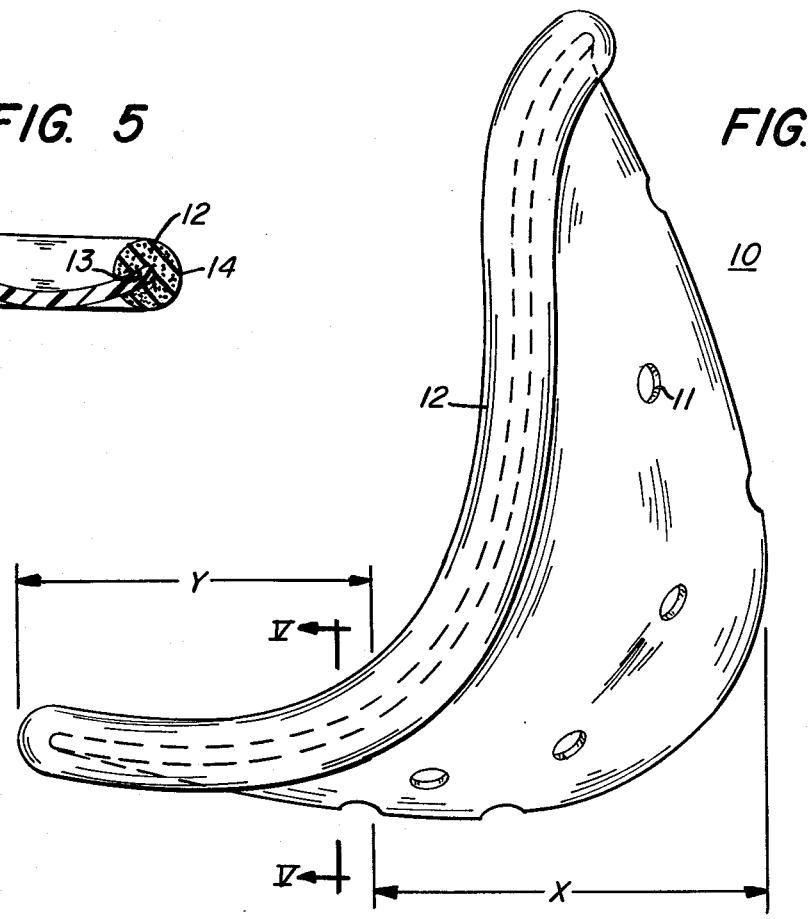
FIG. 5
FIG. 4
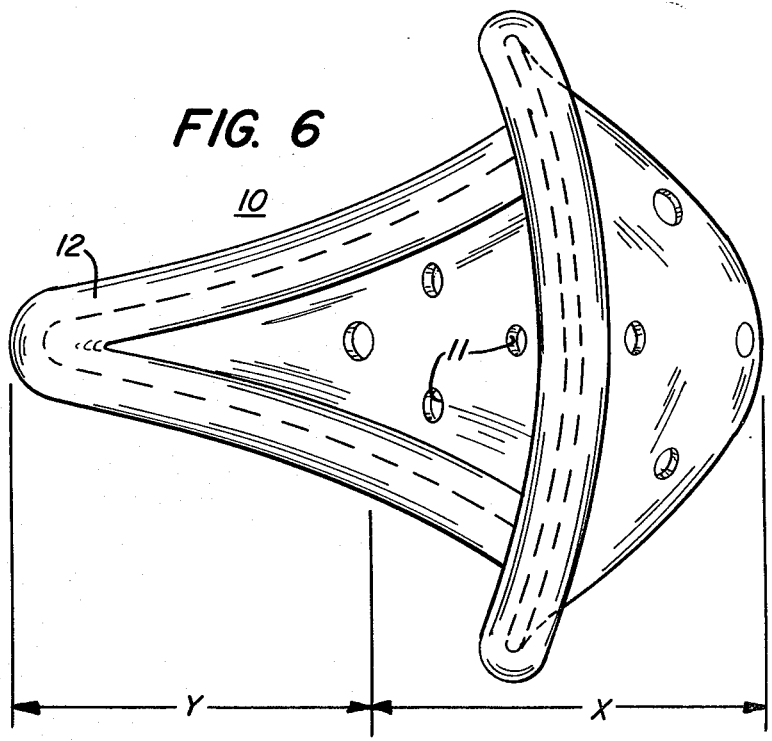
FIG. 6

STRAP FOR A PROTECTIVE DEVICE

CROSS REFERENCE TO RELATED APPLICATIONS

This is a continuation-in-part of application Ser. No. 696,740 filed June 16, 1976, now U.S. Pat. No. 4,043,329.

BACKGROUND OF THE INVENTION

Field of the Invention

This invention relates to protective devices and more particularly to protective devices for the male groin region.

Description of the Prior Art

Devices for the protection of the male groin region are extensively utilized in athletics. Generally, these devices have been limited to the jockstrap used to support the male genitals and the "cup" which is a rigid plastic enclosure used to protect the genitals from impact.

In athletic competition particularly body contact sports such as football, hockey, rugby, soccer and the like a cup is worn by the competitors to avoid injury due to inadvertent blows to the groin area. Many of these inadvertent blows to the groin area direct force perpendicular to the axis of the body (i.e. the spine) and require the cup to absorb such blows. The cup effectively insulates the groin area and associated genitals from these perpendicular blows.

However, when the blow is directed upwardly and substantially parallel with the axis of the body, the protection of the genitals by the cup is hindered since the cup rides upwardly with the force of the blow and the edge of the cup tends to ride on the scrotum and impact the testes. Further, angular upward blows produce the same impediment to cup protection as the upward parallel blows.

Although the cup is somewhat effective in the contact sports hereinbefore described, special problems are encountered when the male groin area must be protected in the pursuit of the marshal arts. In the marshal arts particularly karate and the like, blows are intentionally directed to extremely vulnerable areas of the body and especially the groin. This intentional direction of such groin blows presents particular difficulties when training novices in the marshal arts and in competition. The objective in the training of students is to teach them to direct blows to specific points on the body while controlling the force of the blow so directed to eliminate injury to the opponent. However, due to the inexperience of the novice, controlling of the force of the blow is not always accomplished and the opponent may be struck with a very forceful blow. When the blow is directed to and contacts the genitals and nearby areas, severe injury will be encountered. Although the opponent may wear a conventional cup, the upward character of the blow obviates the protection provided by such cup.

In competition, experts in the marshal arts oppose one another and scoring is contingent on critical blows. A blow to the groin in an upward or angular direction is a high scoring blow. If such a blow is not sufficiently controlled, the receiver of such a blow can be severely injured.

In accordance with the present invention a protective device for the groin area is provided which effectively prevents injury due to both perpendicular, parallel and angular blows to the groin.

BRIEF DESCRIPTION OF THE INVENTION

A protective device is comprised of a rigid cup having sufficient volume to enclose the male genitals. A resilient padding is mounted on the edge of the cup and is adapted to contact the lower body. The resilient padding absorbs the impact experienced by the cup. The resilient padding on the cup edge engages the body proximate to the superior ramii, the inferior ramii and the Ischial ramii of the pelvis with minimal contact with the interior upper thighs. The protective device so constructed causes impact experienced by the cup to be absorbed by the padding and the aforementioned portions of the pelvis. The cup is mounted to the body by a jock strap having a pouch adapted to contain the cup.

BRIEF DESCRIPTION OF THE DRAWINGS

FIG. 4 is a side view of a protective device of the invention partially in section;

FIG. 5 is a cross sectional view taken along the 5—5 line of FIG. 4;

FIG. 6 is a top view of a protective device of the invention partially in section.

DETAILED DESCRIPTION OF THE INVENTION

Figure 1:
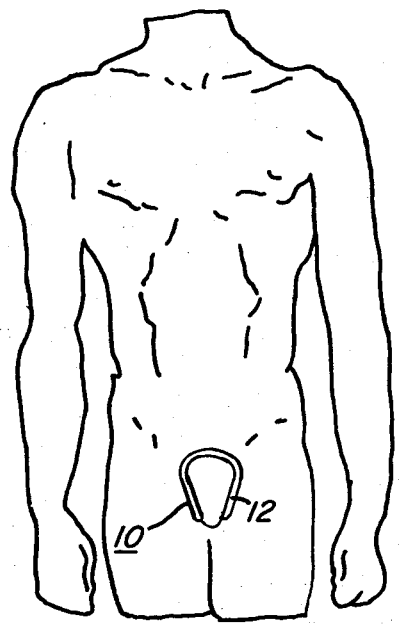
FIG. 1 is a front view of a protective device of the invention being worn by a man.
Figure 2:
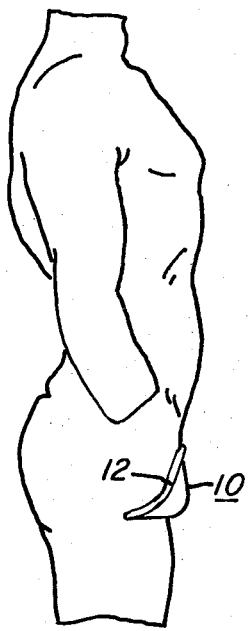
FIG. 2 is a side view of a protective device of the invention being worn by a man.
Figure 3:
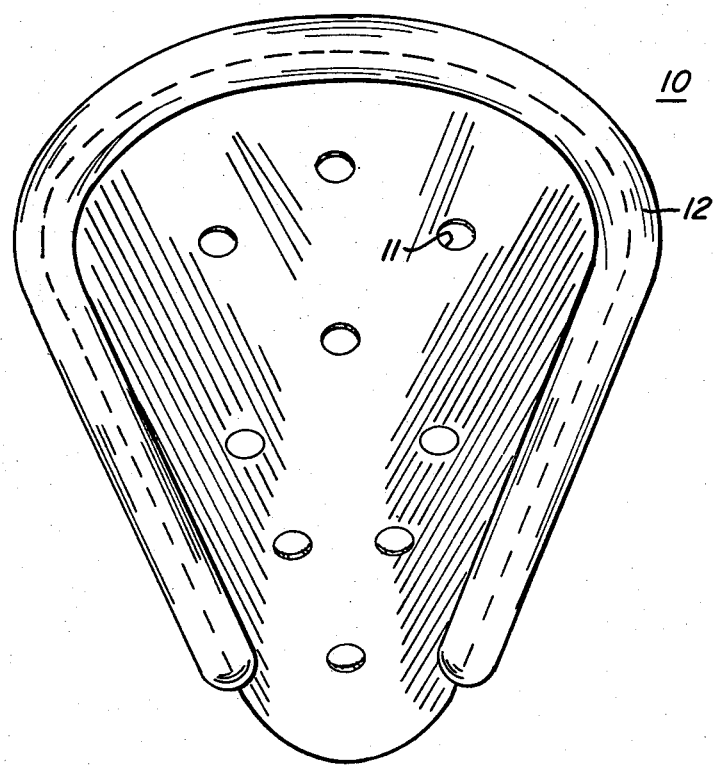
FIG. 3 is a front view of a protective device of the invention partially in section.

Referring now to the drawings in which like reference numerals refer to like parts in the various figures, a cup 10 is constructed of a rigid plastic material. The plastic material of construction of the cup 10 is polypropylene, high density polyethylene or a similar material sufficiently rigid so that the cup retains its shape when impacted. Although virtually any rigid plastic material may be used in the construction of cup 10, care must be taken to insure that the plastic material is sufficiently inert and possesses non-irritating characterisitcs to prevent groin rashes. In one embodiment of the invention the cup 10 is extruded from Hercules GR1 extrusion grade polypropylene. The cup 10 may be extruded, vacuum formed, molded or formed by any suitable process.

A plurality of apertures 11 are provided in cup 10 to afford ventilation to the groin area. Although the apertures 11 are unnecessary as far as protecting the genitals and the area associated therewith, the ventilation makes the protective device more comfortable.

The x portion of cup 10 has sufficient volume to contain the male genitals and the y portion of cup 10 extends between the upper thighs.

Resilient padding 12 is mounted on the edge of cup 10 and is adapted to contact the lower body and absorb impact experienced by the cup 10. The resilient padding 12 is preferably foamed natural rubber, or flexible polyurethane foam. In one embodiment of the invention the resilient padding 12 is Craton Polyfoam flexible foam.

The resilient padding 12 is generally tubular having a slit 13 therein for mounting on the edge of cup 10. If desired the resilient padding 12 may be covered with a sheet of thin plastic 14 such as vinyl polyethylene or the like.

The resilient padding 12 is mounted on the edge of cup 10 to engage the pelvic area proximate to the superior ramii, the interior ramii and the Ischial ramii with minimal contact with the upper thighs. Thus, the resilient padding 12 absorbs some of the impact while the aforementioned portions of the lower pelvis absorb the remainder of the impact.

The y portion of the cup 10 is elongated and narrowing rearwardly thus contouring to the interior of the upper thighs and allowing for freedom of movement. Also the y portion of cup 10 protects the area proximate thereto and prevents the x portion of cup 10 from sliding up and injuring the genitals.

Figure 7:
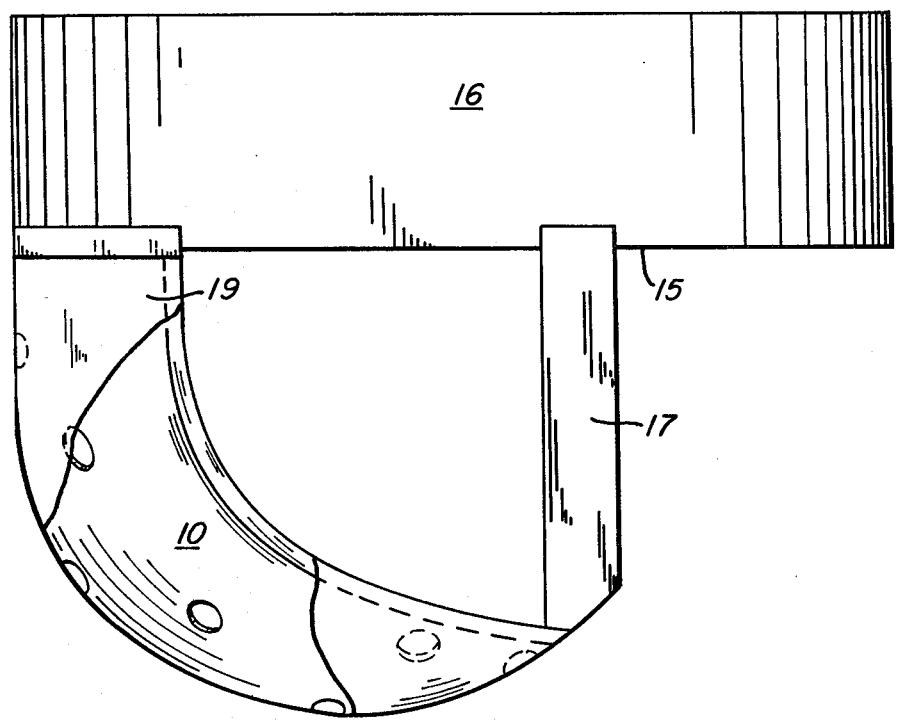
FIG. 7 is a side view of a jock strap with the protective device inserted therein; and, FIG. 8 is a perspective view of the jockstrap shown in FIG. 7.
Figure 8:
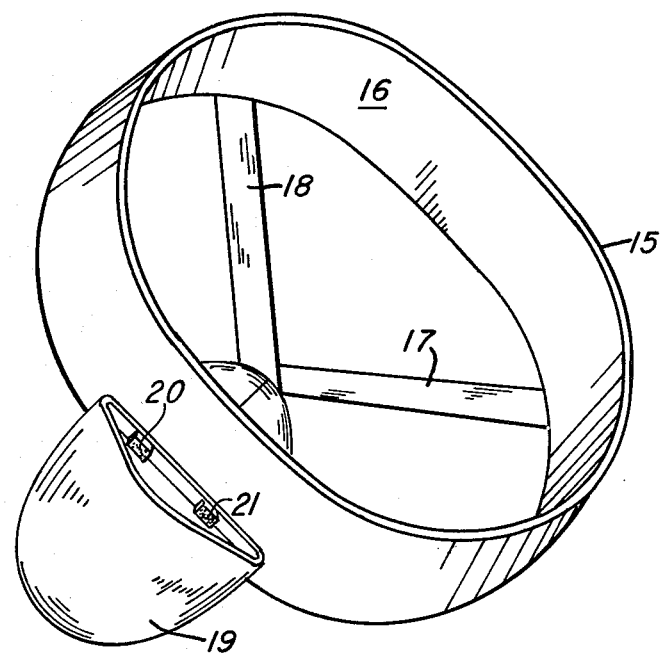

In FIGS. 7 and 8 the jockstrap 15 is shown which is used to mount the cup 10 on the body. The jockstrap 15 has a waist band 16 which is preferably constructed of elastic and provides a tight fit around the waist and/or lower abdomen and the top of the buttocks of the wearer. Two straps 17 and 18 are each connected at one end to the waist band 15 and the two straps 17 and 18 are spaced apart along the waist band 15 to provide an upward tension on the pouch 18 which contains the cup 10. The straps 17 and 18 are joined to the end of pouch 19 at a point near the rectum of the wearer. The straps 17 and 18 are preferably constructed of elastic to impact the necessary tension for stabilizing the cup 10 in the desired anatomical area during physical activity of the wearer. The pouch 19 is attached to the waist band 16 at the opening of the pouch. The attachment of the pouch to the waist band and the pouch to the straps 17 and 18 provide a unitary structure for holding the cup 10 in position.

Two fasteners 20 and 21 are positioned at the opening of the pouch 19 to close the pouch for secure fastening of the cup 10 to the body. The interior of the pouch 19 must be of sufficient volume to contain the cup 10. The pouch 19 should also be constructed so that the holding tension of the pouch is exerted on the side of the cup 10 which is away from the body while having sufficient excess material to contour the pouch to the interior of the cup 10.

Although the protective device is extremely useful in protecting the male groin during the practice of the marshal arts, it may be used for protection in other contact sports. In any event, the protective device of the invention provides greater protection than the conventional cup.

What is claimed is:

1. A jockstrap for holding an athletic cup to the body comprising:
   a waist band;
   two straps, one end of each being attached to the outer circumference of said waist band at points which are to the rear of a vertical line bisecting said waist band as viewed from the side;
   a pouch constructed to hold the athletic cup attached to said straps, said pouch being attached at one end to said straps at a point near the rectum of the wearer which is to the rear of the vertical line bisecting said waist band as viewed from the side, said pouch having an opening to removably insert the athletic cup, said pouch being attached to said waist band at the opening thereof, and said pouch extending from the front of said waist band under the wearer's abdomen and between the wearer's legs to a point near the wearer's rectum; and,
   said jockstrap constructed to hold said cup to the body of a wearer in constant position during physical exercise.

2. The jockstrap of claim 1 including means for closing the pouch after insertion of the cup.

3. The jockstrap of claim 1 wherein said pouch exerts holding tension on the cup on the side of the cup away from the body.

4. A jockstrap for holding a rigid athletic cup, the athletic cup having sufficient volume to enclose the male genitals, the athletic cup having a rearward portion substantially perpendicular to the cup portion extending rearward under the wearer's abdomen and between the wearer's legs to a point near the wearer's rectum, the rearward portion of the athletic cup having convergent edges, said jockstrap comprising:
   a waist band;
   two straps, one end of each being attached to the outer circumference of said waist band at points which are to the rear of a vertical line bisecting said waist band as viewed from the side;
   a pouch constructed to hold the rigid athletic cup, one end of said pouch being attached to the outer circumference of said waist band at the front of said waist band, the other end of said pouch being attached to said straps at a point near the rectum of the wearer, said pouch thereby extending from the front of said waist band underneath the abdomen and between the legs of the wearer to a point near the rectum of the wearer, and said pouch having an opening to removably insert the rigid athletic cup at the point of attachment of said pouch and said waist band; and,
   said jockstrap constructed to hold the athletic cup to the body of a wearer in constant position during physical exercise.

5. A jockstrap as claimed in claim 4 including:
   fastening means for closing the pouch after insertion of the cup.

6. A jockstrap as claimed in claim 5 wherein:
   said pouch exerts holding tension on the cup on the side of the cup which is away from the body.

7. A jockstrap as claimed in claim 6 wherein:
   said straps and said waist band are made of resilient material.

* * * * *